United States Patent
Narabu et al.

(10) Patent No.: US 9,526,462 B2
(45) Date of Patent: Dec. 27, 2016

(54) X-RAY DIAGNOSTIC APPARATUS

(71) Applicant: TOSHIBA MEDICAL SYSTEMS CORPORATION, Otawara-Shi (JP)

(72) Inventors: Yusuke Narabu, Nasushiobara (JP); Tadaharu Kobayashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 352 days.

(21) Appl. No.: 14/337,259

(22) Filed: Jul. 22, 2014

(65) Prior Publication Data

US 2014/0334602 A1 Nov. 13, 2014

Related U.S. Application Data

(63) Continuation of application No. PCT/JP2013/080654, filed on Nov. 13, 2013.

(30) Foreign Application Priority Data

Nov. 13, 2012 (JP) .................. 2012-249775

(51) Int. Cl.
*A61B 6/10* (2006.01)
*A61B 6/04* (2006.01)
*A61B 6/00* (2006.01)

(52) U.S. Cl.
CPC ............. *A61B 6/102* (2013.01); *A61B 6/0407* (2013.01); *A61B 6/0457* (2013.01); *A61B 6/547* (2013.01); *A61B 6/107* (2013.01); *A61B 6/4441* (2013.01)

(58) Field of Classification Search
CPC ..... A61B 6/0407; A61B 6/0457; A61B 6/102; A61B 6/107; A61B 6/4441; A61B 6/547; A61B 6/4464; A61B 6/032; A61B 6/06; A61B 6/12; A61B 6/469; A61B 6/0442; A61B 6/4085; A61B 6/461; A61B 6/487; A61B 6/541; A61B 6/542; A61B 6/405; A61B 6/4435; A61B 6/545; A61B 6/582; A61B 6/586; A61B 6/08; A61B 6/446; A61B 6/587

(Continued)

(56) References Cited

U.S. PATENT DOCUMENTS

2002/0090058 A1* 7/2002 Yasuda .................. A61B 6/08
378/205
2004/0170255 A1 9/2004 Akutsu et al.
(Continued)

FOREIGN PATENT DOCUMENTS

JP 2002-238888 A 8/2002
JP 2003-305064 A 10/2003
(Continued)

OTHER PUBLICATIONS

International Search Report issued on Dec. 10, 2013 for PCT/JP2013/080654 filed on Nov. 13, 2013 with English Translation.
(Continued)

*Primary Examiner* — Irakli Kiknadze
(74) *Attorney, Agent, or Firm* — Oblon, McClelland, Maier & Neustadt, L.L.P.

(57) ABSTRACT

An X-ray diagnostic apparatus includes an imaging unit, a moving mechanism unit, a modeling unit and a mechanism controller. The imaging unit includes an X-ray generating device which generates X-rays for irradiation of an object put on a table-top and an X-ray detecting device which detects the X-rays. The moving mechanism unit moves the table-top and the imaging unit. The modeling unit displays a table-top model representing the table-top and an imaging unit model representing the imaging unit on a display unit, and moves at least one of the table-top model and the imaging unit model on the display unit, in response to an operation of moving at least one of the table-top model and the imaging unit model. The mechanism controller controls the moving mechanism unit to move the table-top and the imaging unit in accordance with positions of the table-top model and the imaging unit model.

8 Claims, 12 Drawing Sheets

(58) Field of Classification Search
USPC .......................................... 378/4, 8, 62, 205
See application file for complete search history.

(56) References Cited

U.S. PATENT DOCUMENTS

2006/0269039 A1* 11/2006 Raupach ................ A61B 6/032
                                                                  378/16
2012/0243655 A1*  9/2012 Ninomiya .............. A61B 6/027
                                                                   378/8

FOREIGN PATENT DOCUMENTS

| JP | 2004-275745 A | 10/2004 |
| JP | 2006-51403 A  |  2/2006 |
| JP | 2008-86372 A  |  4/2008 |
| JP | 2009-22602 A  |  2/2009 |
| JP | 2009-219552 A | 10/2009 |

OTHER PUBLICATIONS

English translation of the International Preliminary Report on Patentability and Written Opinion issued on May 19, 2015 in PCT/JP2013/080654.

* cited by examiner

X-RAY DIAGNOSTIC APPARATUS

CROSS-REFERENCE TO RELATED APPLICATION

This application is a Continuation Application of No. PCT/JP2013/80654, filed on Nov. 13, 2013, and the PCT application is based upon and claims the benefit of priority from Japanese Patent Application No. 2012-249775, filed on Nov. 13, 2012, the entire contents of which are incorporated herein by reference.

FIELD

An embodiment of the present invention relates to an X-ray diagnostic apparatus that prevents interference between a table-top on which an object is put and an imaging unit configured to image the object.

BACKGROUND

In recent years, X-ray diagnostic apparatuses have made progress mainly in circulatory organ fields along with development of angiographic examination and interventional radiology (IVR) using catheters. Such an X-ray diagnostic apparatus includes a table-top on which an object is put. The X-ray diagnostic apparatus further includes an imaging unit including: an X-ray generating device configured to irradiate the object put on the table-top with X-rays; an X-ray detecting device configured to detect X-rays that have been transmitted through the object; and an arm configured to hold the X-ray generating device and the X-ray detecting device. Then, the table-top and the imaging unit are moved by an operation of an operator to respective imaging positions at which imaging of the object is possible, whereby the object is imaged at various angles.

Unfortunately, when the table-top and the imaging unit are moved, in order to avoid interference between the table-top and the imaging unit in an area outside of a field of view of the operator, a person other than the operator needs to visually check positions of the table-top and the imaging unit. Hence, the work is troublesome.

An embodiment, which has been made in order to solve the above-mentioned problem, has an object to provide an X-ray diagnostic apparatus capable of achieving a reduction in work.

BRIEF DESCRIPTION OF THE DRAWINGS

In accompanying drawings.

DETAILED DESCRIPTION

Hereinafter, an embodiment is described with reference to the drawings.

To solve the above-described problems, the present embodiments provide the X-Ray diagnostic apparatus, including: an imaging unit including an X-ray generating device configured to generate X-rays for irradiation of an object-put on a table-top and an X-ray detecting device configured to detect the X-rays; a moving mechanism unit configured to move the table-top and the imaging unit; a modeling unit configured to display a table-top model representing the table-top and an imaging unit model representing the imaging unit on a display unit, and to move at least one of the table-top model and the imaging unit model on the display unit, in response to an operation of moving at least one of the table-top model and the imaging unit model; and a mechanism controller configured to control the moving mechanism unit to move the table-top and the imaging unit in accordance with positions of the table-top model and the imaging unit model.

Figure 1:
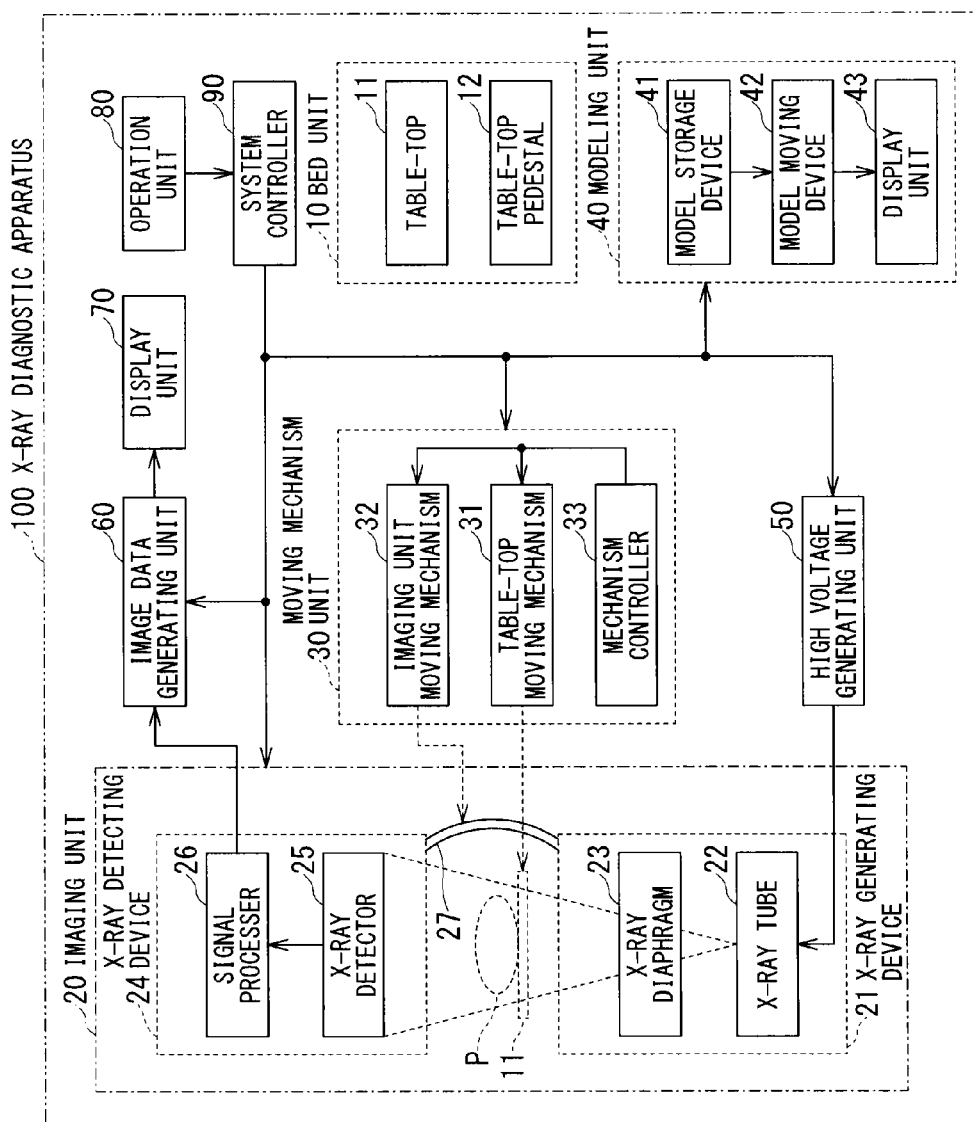
FIG. 1 is a block diagram showing a configuration of an X-ray diagnostic apparatus according to a present embodiment.

FIG. 1 is a block diagram showing a configuration of an X-ray diagnostic apparatus according to a present embodiment. An X-ray diagnostic apparatus 100 according to the present embodiment includes: a bed unit 10 on which an object P is put; an imaging unit 20 configured to irradiate the object P put on the bed unit 10 with X-rays and image the object P; a moving mechanism unit 30 configured to move the bed unit 10 and the imaging unit 20; a modeling unit 40 configured to display models (reference signs "10a" and "20a" in FIG. 3) representing the bed unit 10 and the imaging unit 20; and a high voltage generating unit 50 configured to generate a high voltage necessary for the X-ray irradiation of the imaging unit 20.

The X-ray diagnostic apparatus 100 further includes: an image data generating unit 60 configured to generate image data on the basis of an imaging result of the imaging unit 20; a display unit 70 configured to display the image data generated by the image data generating unit 60; an operation unit 80 configured to input various commands and other operations; and a system controller 90 configured to control the above-mentioned units.

The bed unit 10 is installed in an imaging room covered by a shield material that prevents X-rays from leaking to the outside. Then, the bed unit 10 includes: a table-top 11 on which the object P is put; and a table-top pedestal 12 configured to movably support the table-top 11.

The imaging unit 20 is installed in the imaging room, and is arranged so as to be movable with respect to the bed unit 10. Then, the imaging unit 20 includes: an X-ray generating device 21 configured to generate X-rays; an X-ray detecting device 24 configured to detect the X-rays; and an arm 27 configured to hold the X-ray generating device 21 at its one end and hold the X-ray detecting device 24 at its another end.

The X-ray generating device 21 includes: an X-ray tube 22 configured to generate X-rays for irradiation of the object P put on the table-top 11 of the bed unit 10; and an X-ray diaphragm 23 configured to restrict an irradiation range of the X-rays that come from the X-ray tube 22 for the irradiation of the object P.

The X-ray detecting device 24 is arranged so as to be opposed to the X-ray generating device 21. Then, the X-ray detecting device 24 includes: an X-ray detector 25 configured to detect X-rays that have been transmitted through the object P on the table-top 11; and a signal processor 26 configured to process a detection signal detected by the X-ray detector 25 and generate X-ray projection data.

The moving mechanism unit 30 includes: a table-top moving mechanism 31 that is configured to move the table-top 11 of the bed unit 10 and is arranged on the table-top pedestal 12; an imaging unit moving mechanism 32 that is configured to move the imaging unit 20 and is arranged in the imaging room; and a mechanism controller 33 configured to control the table-top moving mechanism 31 and the imaging unit moving mechanism 32.

Figure 2:
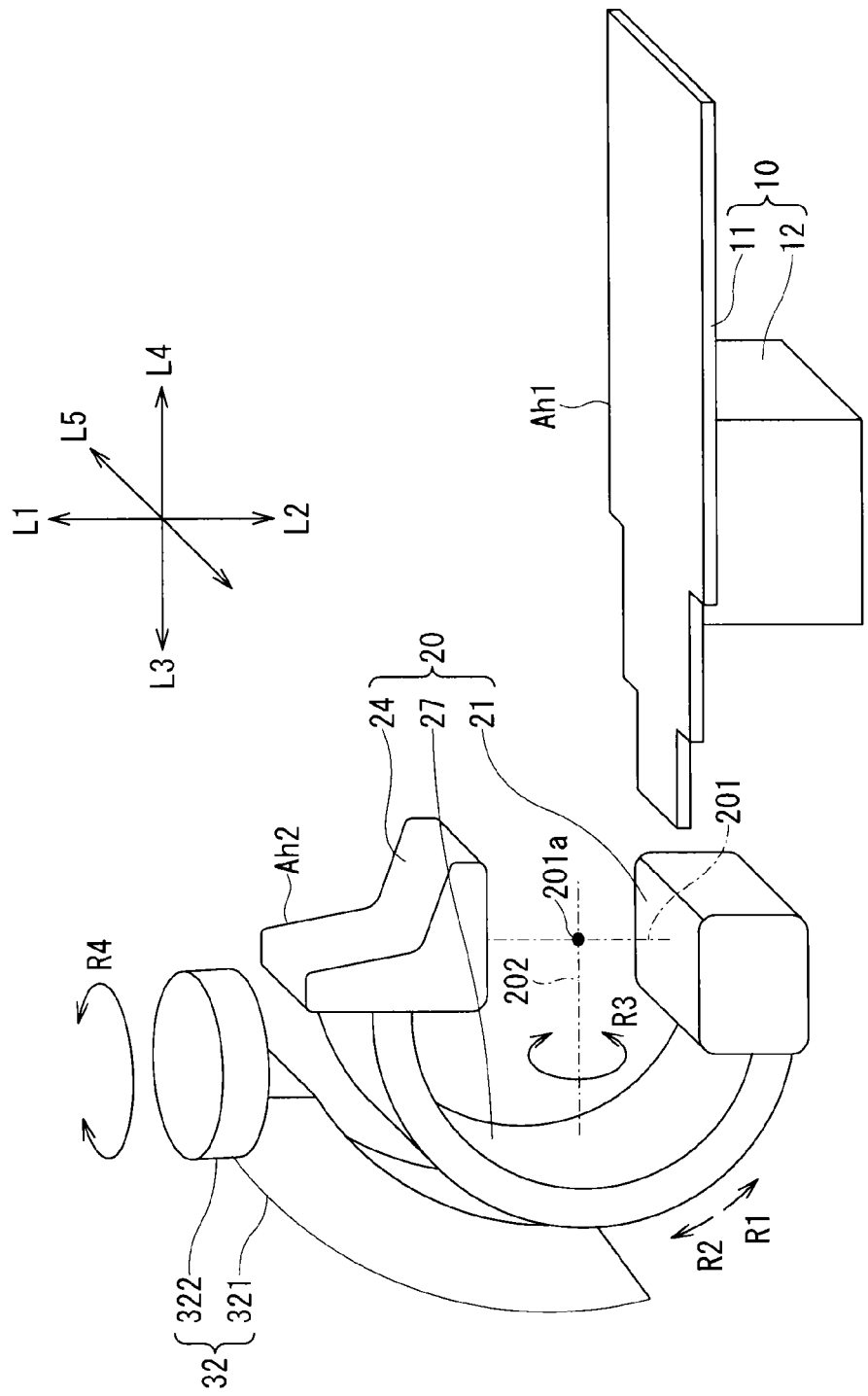
FIG. 2 is a diagram showing example moving directions of a table-top and an imaging unit.

FIG. 2 is a diagram showing example moving directions of the table-top 11 and the imaging unit 20. The table-top 11 and the imaging unit 20 are respectively stopped at positions Ah1 and Ah2. Then, the table-top moving mechanism 31 moves the table-top 11 in an arrow L1 direction that is an upper direction and an arrow L2 direction that is a lower direction. The table-top moving mechanism 31 also moves the table-top 11 in an arrow L3 direction that is a direction toward the imaging unit 20 in a longitudinal direction of the table-top 11 and an arrow L4 direction opposite to the L3 direction. The table-top moving mechanism 31 also moves the table-top 11 in an arrow L5 direction that is a lateral direction of the table-top 11. The table-top moving mechanism 31 tilts the table-top 11 in the longitudinal direction and the lateral direction.

The imaging unit moving mechanism 32 includes: a first supporter 321 configured to turnably support the arm 27 of the imaging unit 20; and a second supporter 322 that is configured to turnably support the first supporter 321 and is arranged in the vicinity of a ceiling of the imaging room. Then, along with a turn of the arm 27 about a turn center 201a located on a straight line 201 passing through centers of the X-ray generating device 21 and the X-ray detecting device 24, the imaging unit 20 is moved in an arrow R1 direction and an arrow R2 direction opposite to the R1 direction. Along with a turn of the arm 27 about a straight line 202 (as a turning axis) that perpendicularly intersects with the straight line 201 at the turn center 201a, the imaging unit 20 is also moved in an arrow R3 direction. Along with a turn of the first supporter 321, the imaging unit 20 is also moved in an arrow R4 direction. Along with a movement of the second supporter 322, the imaging unit 20 is moved in the L3 direction, the L4 direction, and the L5 direction.

The mechanism controller 33 (shown in FIG. 1) includes a detector (not shown) configured to detect a position of the table-top 11 that has been moved in the L1 direction, the L2 direction, the L3 direction, the L4 direction, and the L5 direction and a position of the table-top 11 that has been tilted in the longitudinal direction and the lateral direction. The mechanism controller 33 (shown in FIG. 1) further includes a detector (not shown) configured to detect a position of the imaging unit 20 that has been moved in the R1 direction, the R2 direction, the R3 direction, the R4 direction, the L3 direction, the L4 direction, and the L5 direction.

Returning to the description of FIG. 1, the modeling unit 40 includes a model storage device 41 configured to store a three-dimensional bed unit model and a three-dimensional imaging unit model respectively representing the bed unit 10 and the imaging unit 20 on the basis of actual dimensions thereof.

Figure 3:
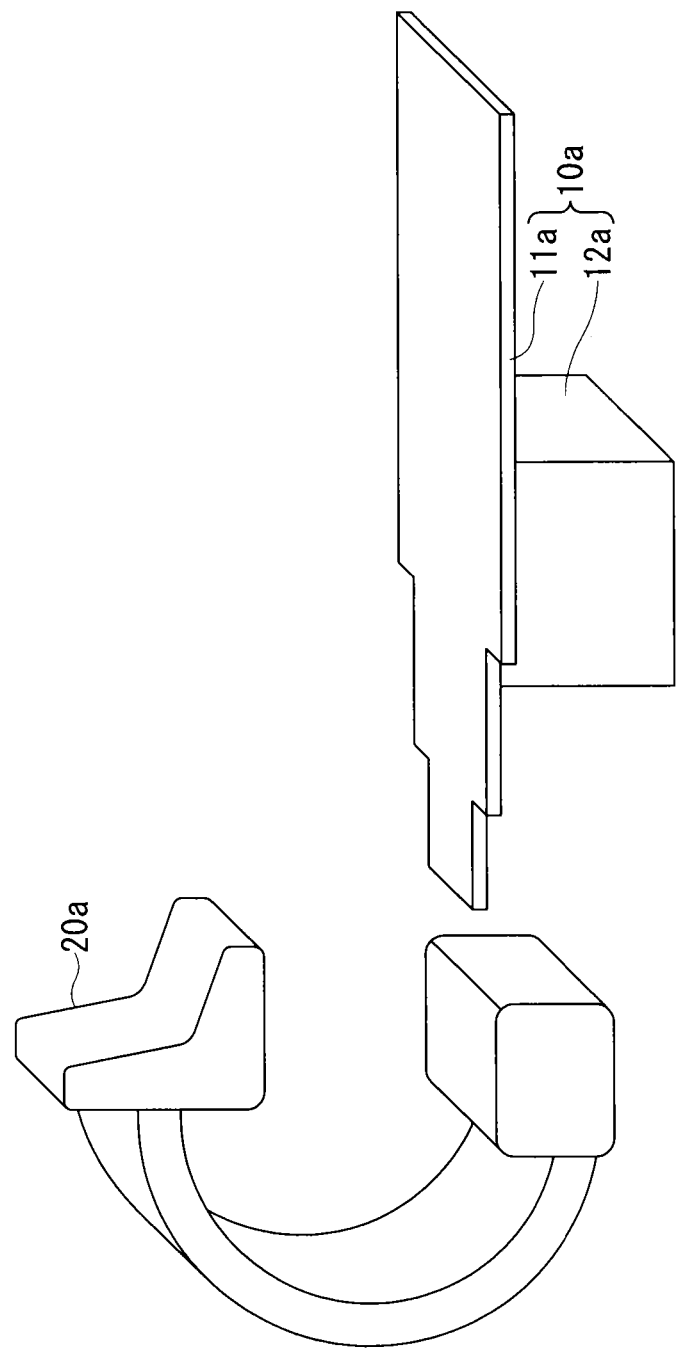
FIG. 3 is a diagram showing examples of a bed unit model and an imaging unit model stored in a model storage device.

FIG. 3 is a diagram showing examples of the bed unit model and the imaging unit model stored in the model storage device 41. FIG. 3 illustrates the three-dimensional bed unit model 10a and the three-dimensional imaging unit model 20a respectively representing the bed unit 10 and the imaging unit 20 (both shown in FIG. 1) on the basis of the actual dimensions thereof. The bed unit model 10a includes a three-dimensional table-top model 11a and a three-dimensional table-top pedestal model 12a respectively representing the table-top 11 and the table-top pedestal 12 (both shown in FIG. 1) on the basis of actual dimensions thereof.

Returning to the description of FIG. 1, the modeling unit 40 further includes a model moving device 42 configured to read the bed unit model 10a and the imaging unit model 20a out of the model storage device 41 and arrange and move the bed unit model 10a and the imaging unit model 20a in a virtual space. The modeling unit 40 further includes a display unit 43 that is arranged in the vicinity of the operation unit 80 and is configured to display the bed unit model 10a and the imaging unit model 20a that have been arranged and moved in the virtual space by the model moving device 42. The bed unit model 10a and the imaging unit model 20a may be displayed on the display unit 70.

If a selection instruction of an automatic mode is input from the operation unit 80 and then movement instructions of the table-top model 11a and the imaging unit model 20a (both shown in FIG. 3) are input from the operation unit 80, the model moving device 42 moves the table-top model 11a and the imaging unit model 20a in the virtual space in directions corresponding to moving directions of the table-top 11 and the imaging unit 20. Subsequently, if an automatic positioning instruction is input from the operation unit 80, the moving mechanism unit 30 moves the table-top 11 to an actual-space position corresponding to a virtual-space position of the table-top model 11a, in response to the movement instruction for moving the table-top model 11a, and the moving mechanism unit 30 moves the imaging unit 20 to an actual-space position corresponding to a virtual-space position of the imaging unit model 20a, in response to the movement instruction for moving the imaging unit model 20a.

Otherwise, if a selection instruction of a manual mode is input from the operation unit 80 and then movement instructions of the table-top 11 and the imaging unit 20 are input from the operation unit 80, the moving mechanism unit 30 moves the table-top 11 and the imaging unit 20. In conjunction with the movement of the table-top 11 and the imaging unit 20, the model moving device 42 moves the table-top model 11a and the imaging unit model 20a (both shown in FIG. 3) to virtual-space positions corresponding to positions of the table-top 11 and the imaging unit 20.

The high voltage generating unit 50 includes: a high voltage generating unit (not shown) configured to supply a high voltage to the X-ray tube 22 of the X-ray generating device 21 in the imaging unit 20; and an X-ray controlling unit (not shown) configured to control the high voltage generating unit. Then, the high voltage generating unit 50 supplies a high voltage for generating X-rays to the X-ray tube 22, on the basis of irradiation conditions including a tube voltage and a tube current supplied by the system controller 90.

The image data generating unit 60 generates image data on the basis of X-ray projection data that is generated by the signal processer 26 of the X-ray detecting device 24 as a result of X-ray irradiation of the object P by the imaging unit 20. The display unit 70 includes a monitor with a liquid crystal panel or a cathode ray tube (CRT), and displays the image data generated by the image data generating unit 60.

The operation unit 80 includes input devices (not shown) such as a keyboard, a trackball, a joystick, a mouse, and a switch. Then, the operation unit 80 inputs, for example: an instruction for setting X-ray irradiation conditions; an instruction for starting X-ray irradiation (imaging start); an instruction for stopping X-ray irradiation (imaging stop); an instruction for moving the table-top 11 of the bed unit 10 and the imaging unit 20; and an instruction for moving the table-top model 11a of the bed unit model 10a and the imaging unit model 20a (both shown in FIG. 3).

The system controller 90 includes a central processing unit (CPU) and a memory circuit (both not shown). Then, the system controller 90 temporarily stores input information input from the operation unit 80, and then performs overall control on the imaging unit 20, the moving mechanism unit 30, the modeling unit 40, the high voltage generating unit 50, and the image data generating unit 60 on the basis of the input information. Then, the system controller 90 performs such control that associates positions of one of: the table-top 11 of the bed unit 10 and the imaging unit 20; and the table-top model 11a of the bed unit model 10a and the imaging unit model 20a (both shown in FIG. 3), with positions of another thereof.

Hereinafter, with reference to FIG. 1 to FIG. 12, description is given of an example operation of the X-ray diagnostic apparatus 100 when the table-top 11 of the bed unit 10 and the imaging unit 20 are moved to imaging positions at which imaging of an affected area of the object P is possible.

First, the following example is described with reference to FIG. 1 to FIG. 10. That is, the selection instruction of the automatic mode is input from the operation unit 80, and then: the movement instructions of the table-top model 11a and the imaging unit model 20a of the modeling unit 40 into respective imaging positions in a virtual space are input from the operation unit 80; and the automatic positioning instruction is input from the operation unit 80. In response thereto, the imaging unit 20 is moved to an imaging position in an actual space corresponding to the imaging position in the virtual space.

Figure 4:
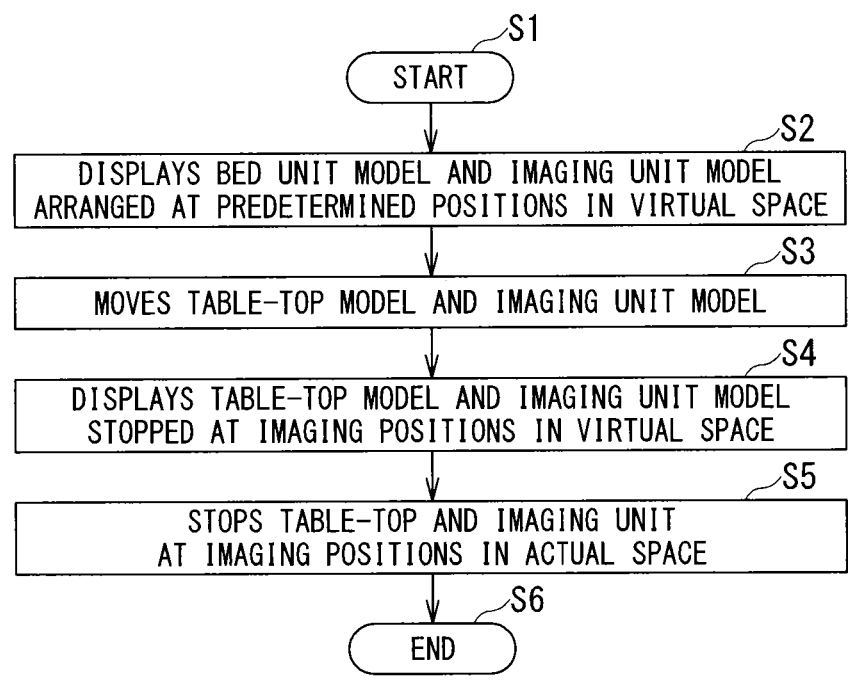
FIG. 4 is a flow chart showing an operation of the X-ray diagnostic apparatus according to the present embodiment.

FIG. 4 is a flow chart showing an operation of the X-ray diagnostic apparatus 100 according to the present embodiment.

If a display instruction of the bed unit model 10a and the imaging unit model 20a stored in the model storage device 41 of the modeling unit 40 on the display unit 43 is input from the operation unit 80, the X-ray diagnostic apparatus 100 starts the operation (Step S1).

The system controller 90 instructs the modeling unit 40 to display the bed unit model 10a and the imaging unit model 20a. The model moving device 42 of the modeling unit 40 reads the bed unit model 10a and the imaging unit model 20a out of the model storage device 41. Then, the model moving device 42 respectively arranges the bed unit model 10a and the imaging unit model 20a at predetermined positions in the virtual space corresponding to the positions Ah1 and Ah2 (shown in FIG. 2) of the table-top 11 of the bed unit 10 and the imaging unit 20, and outputs the result to the display unit 43. The display unit 43 displays the bed unit model 10a and the imaging unit model 20a arranged at the predetermined positions in the virtual space (Step S2).

Figure 5:
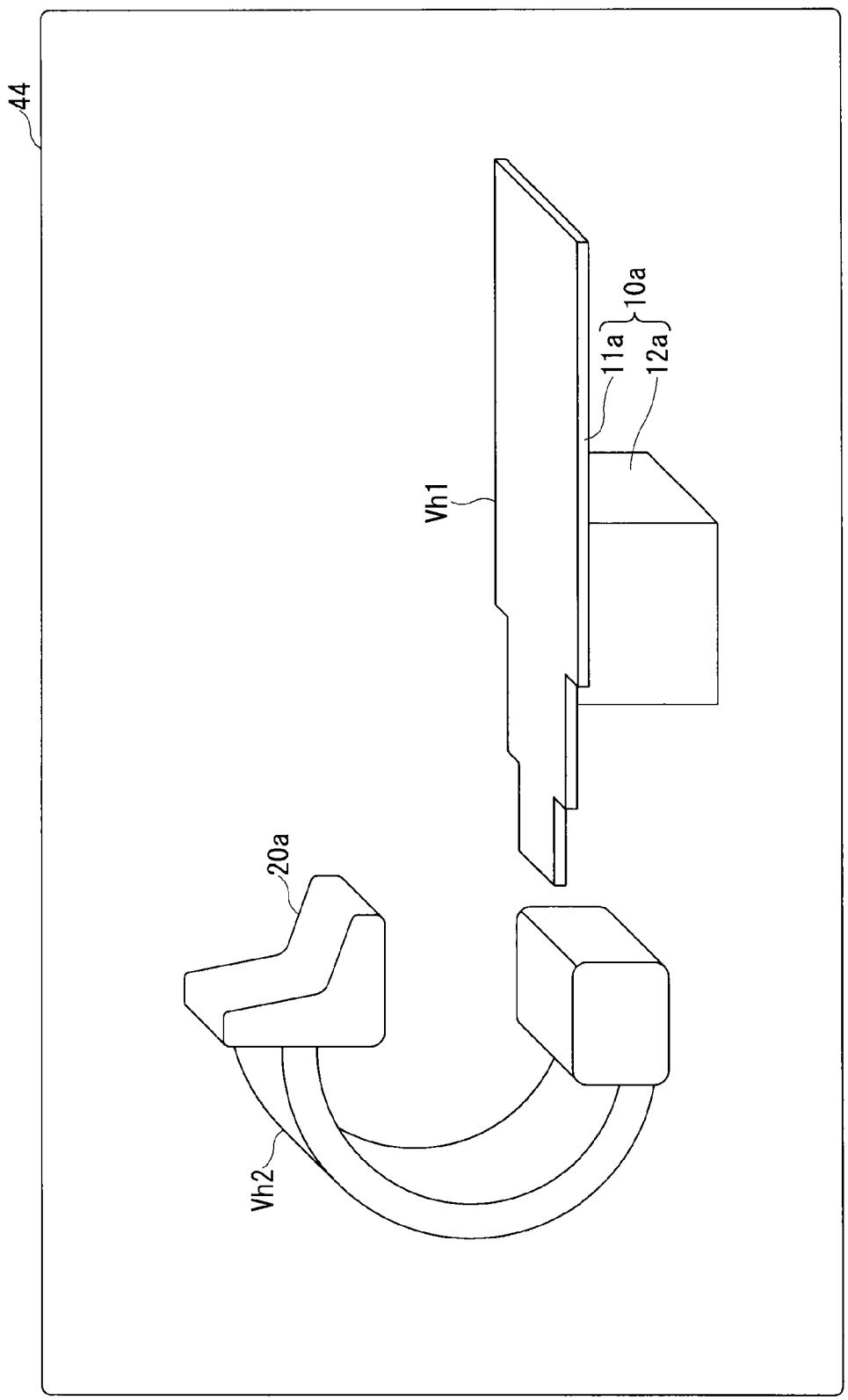
FIG. 5 is a diagram showing an example screen of a display unit on which the bed unit model and the imaging unit model arranged at predetermined positions are displayed.

FIG. 5 is a diagram showing an example screen of the display unit 43 on which the bed unit model 10a and the imaging unit model 20a arranged at the predetermined positions are displayed. The bed unit model 10a and the imaging unit model 20a are displayed on this screen 44. Then, the table-top model 11a is arranged at a position Vhf in the virtual space corresponding to the position Ah1 (shown in FIG. 2) of the table-top 11 so as to be movable with respect to the table-top pedestal model 12a. The imaging unit model 20a is arranged at a position Vh2 in the virtual space corresponding to the position Ah2 (shown in FIG. 2) of the imaging unit 20 so as to be movable with respect to the table-top pedestal model 12a.

In this way, the three-dimensional bed unit model 10a and the three-dimensional imaging unit model 20a respectively representing the bed unit 10 and the imaging unit 20 can be displayed on the display unit 43.

Returning to the description of FIG. 4, if the selection instruction of the automatic mode is input from the operation unit 80, and then movements of the table-top model 11a and the imaging unit model 20a from the respective positions Vh1 and Vh2 to the imaging positions are input from the operation unit 80, the model moving device 42 moves the table-top model 11a and the imaging unit model 20a arranged at the positions Vh1 and Vh2 (Step S3 in FIG. 4).

In this example, the model moving device 42 moves the table-top model 11a from the position Vh1 in a direction corresponding to the L1 direction in the actual space, and further moves the table-top model 11a in a direction corresponding to the L3 direction in the actual space. The model moving device 42 moves the imaging unit model 20a from the position Vh2 in a direction corresponding to the R1 direction in the actual space.

In response to the movement instructions of the table-top model 11a and the imaging unit model 20a, the model moving device 42 outputs the table-top model 11a and the imaging unit model 20a that have been moved from the positions Vh1 and Vh2, to the display unit 43. The display unit 43 displays in real time the table-top model 11a and the imaging unit model 20a that have been moved from the positions Vh1 and Vh2.

In response to a stopping instruction, input from the operation unit 80, of the table-top model 11a and the imaging unit model 20a, the model moving device 42 stops the table-top model 11a and the imaging unit model 20a at the imaging positions in the virtual space. The display unit 43 displays the table-top model 11a and the imaging unit model 20a stopped at the imaging positions in the virtual space (Step S4 in FIG. 4).

Figure 6:
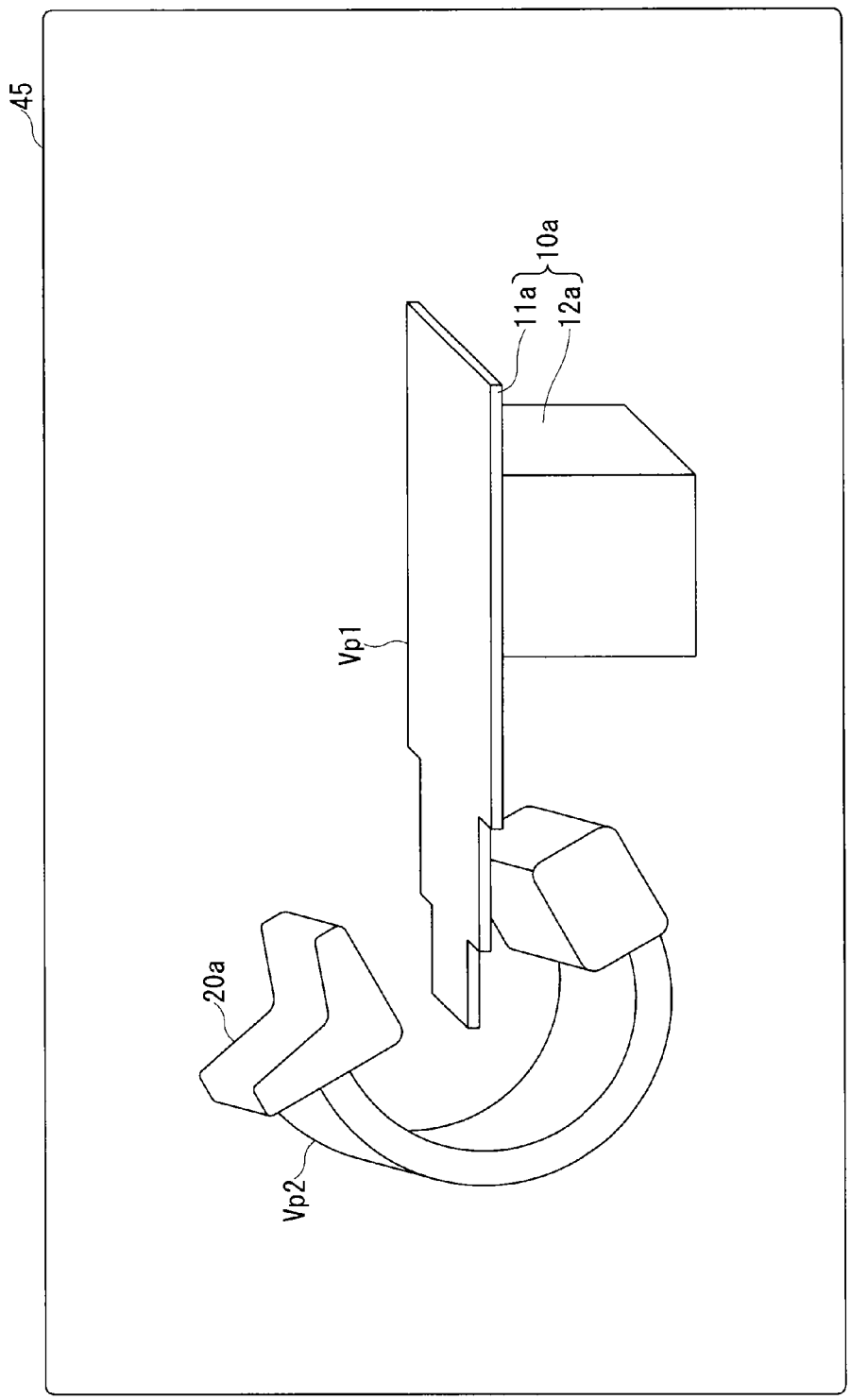
FIG. 6 is a diagram showing an example screen of the display unit on which the table-top model and the imaging unit model arranged at an imaging positions are displayed.

FIG. 6 is a diagram showing an example screen of the display unit 43 on which the table-top model 11a and the imaging unit model 20a arranged at the imaging positions are displayed. The table-top model 11a that has been moved from the position Vh1 and stopped at an imaging position Vp1 and the imaging unit model 20a that has been moved from the position Vh2 and stopped at an imaging position Vp2 are displayed on this screen 45.

Here, if a setting instruction of points of view and thus a display instruction of the table-top model 11a and the imaging unit model 20a arranged at the imaging positions Vp1 and Vp2 in the virtual space from a plurality of directions are input from the operation unit 80, the display unit 43 displays the table-top model 11a and the imaging unit model 20a arranged at the imaging positions Vp1 and Vp2 from the plurality of directions.

In this way, the table-top model 11a and the imaging unit model 20a can be moved to the imaging positions Vp1 and Vp2 in the virtual space. Then, because the table-top model 11a and the imaging unit model 20a arranged at the imaging positions Vp1 and Vp2 are displayed from the plurality of directions on the display unit 43, an operator can check whether or not the table-top model 11a and the imaging unit model 20a arranged at the imaging positions Vp1 and Vp2 in the virtual space interfere with each other.

If observation of the table-top model 11a and the imaging unit model 20a at the imaging positions Vp1 and Vp2 displayed on the display unit 43 proves that the table-top model 11a and the imaging unit model 20a are spaced apart from each other at appropriate positions, the automatic positioning instruction is input from the operation unit 80.

In response to the automatic positioning instruction, the model moving device 42 outputs, for example, the moving order in the virtual space, the moving directions, and the positional information after the movement of the table-top model 11a and the imaging unit model 20a arranged at the imaging positions Vp1 and Vp2 in the virtual space, to the system controller 90.

On the basis of the moving order, the moving directions, and the positional information after the movement outputted by the model moving device 42, the system controller 90 determines a movement plan including the moving order in the actual space, the moving directions, and the positional information after the movement of the table-top 11 and the imaging unit 20. Then, the system controller 90 outputs information of the determined movement plan to the mechanism controller 33 of the moving mechanism unit 30. On the basis of the movement plan outputted by the system controller 90, the mechanism controller 33 controls the table-top moving mechanism 31 and the imaging unit moving mechanism 32. Then, the mechanism controller 33 moves the table-top 11 and the imaging unit 20.

Figure 7:
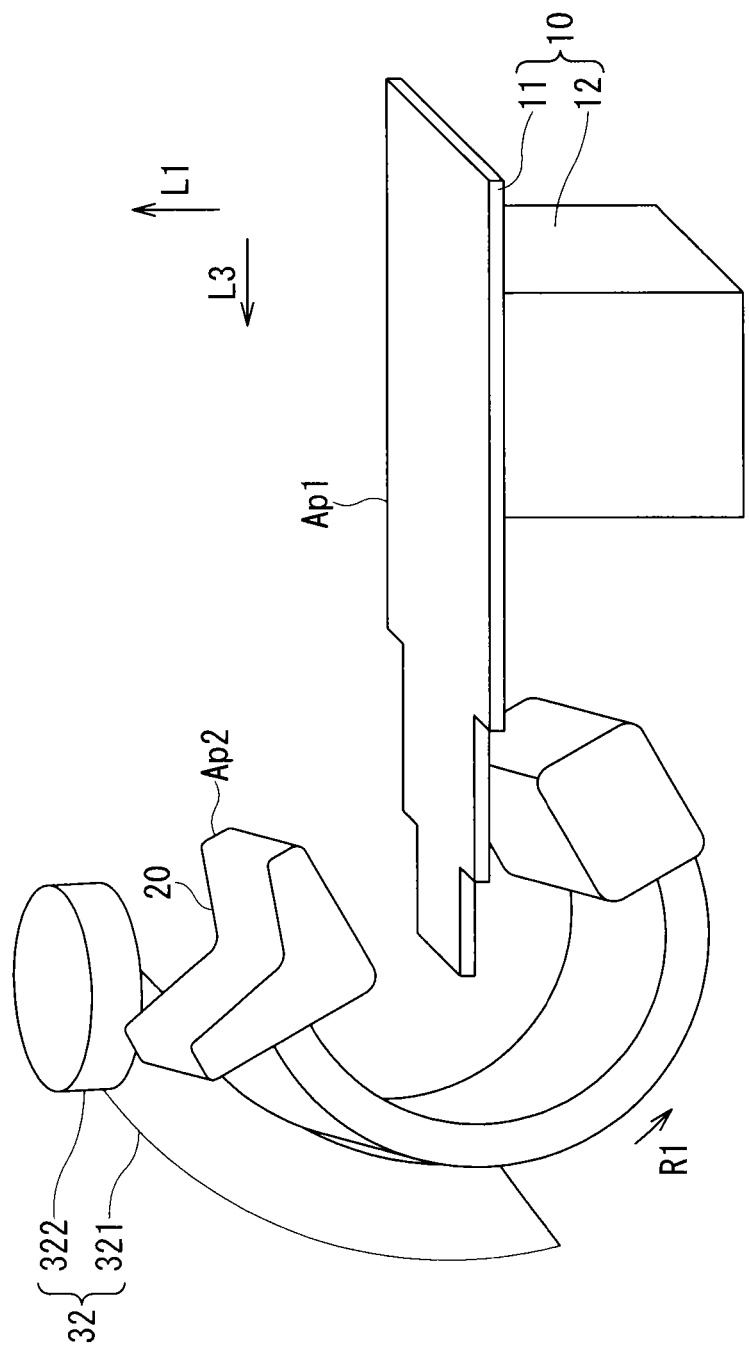
FIG. 7 is a diagram showing the table-top and the imaging unit stopped at the imaging positions in an actual space.

The table-top moving mechanism 31 moves the table-top 11 from the position Ah1 in the L1 direction, and further moves the table-top 11 in the L3 direction. The imaging unit moving mechanism 32 moves the imaging unit 20 from the position Ah2 in the R1 direction. Then, as shown in FIG. 7, the table-top 11 is stopped at an imaging position Ap1 in the actual space corresponding to the imaging position Vp1 in the virtual space, and the imaging unit 20 is stopped at an imaging position Ap2 in the actual space corresponding to the imaging position Vp2 in the virtual space (Step S5 in FIG. 4). FIG. 7 is a diagram showing the table-top and the imaging unit stopped at the imaging positions in the actual space.

In Steps S2 and S4, in addition to the table-top model 11a and the imaging unit model 20a, the model moving device 42 may display a virtual interference region corresponding to a three-dimensional interference region (patient barrier region) in the vicinity of the table-top 11, in the vicinity of the table-top model 11a on the display unit 43.

Figure 8:
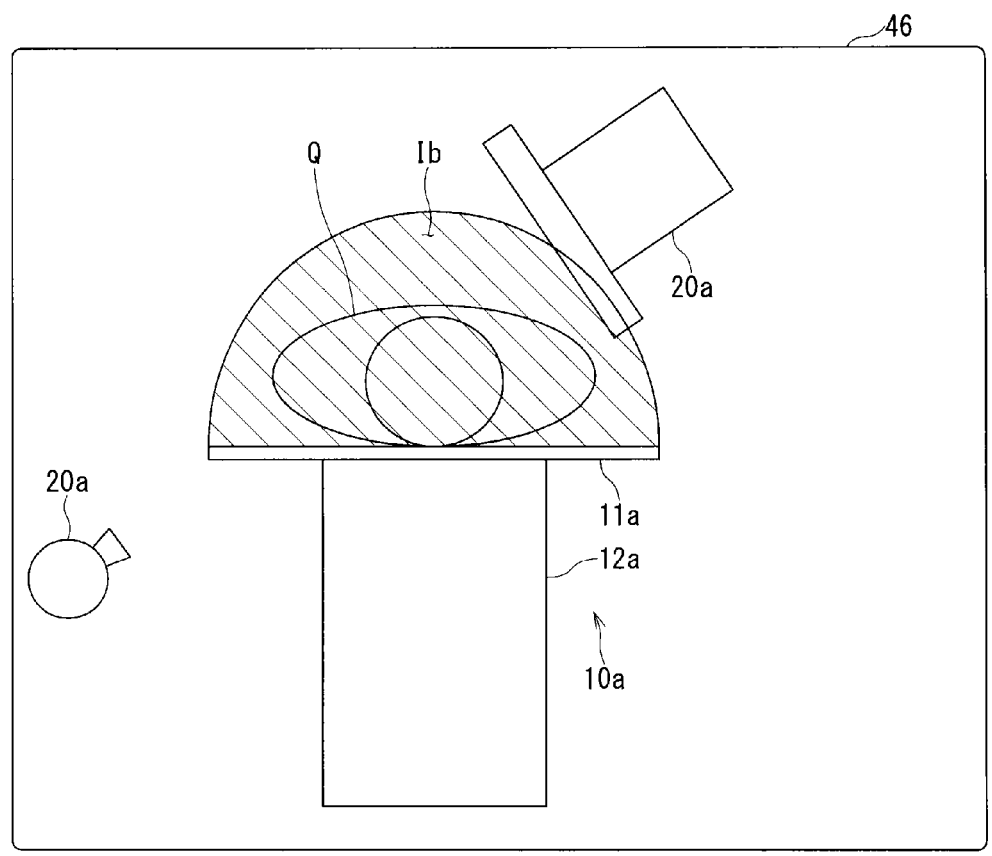
FIG. 8 is a diagram showing an example screen of the display unit on which the bed unit model and the imaging unit model arranged at the predetermined positions and a virtual interference region are displayed.

FIG. 8 is a diagram showing an example screen of the display unit 43 on which the bed unit model 10a and the imaging unit model 20a arranged at the predetermined positions and the virtual interference region are displayed. The bed unit model 10a and the imaging unit model 20a are displayed on this screen 46. A semicircular columnar virtual interference region Ib corresponding to a semicircular columnar (whose axis extends in a direction corresponding to the L3-L4 direction in FIG. 2) interference region (patient barrier region) on the table-top 11 is displayed on the table-top model 11a. Then, the table-top model 11a is arranged at a virtual-space position corresponding to the position of the table-top 11 so as to be movable with respect to the table-top pedestal model 12a. The imaging unit model 20a is arranged at a virtual-space position corresponding to the position of the imaging unit 20 so as to be movable with respect to the table-top pedestal model 12a.

An object Q in the virtual space corresponding to the object P (shown in FIG. 1) may be displayed on the screen 46. In response to an operation of the operator, the display unit 43 can three-dimensionally rotate the bed unit model 10a, the imaging unit model 20a, and the virtual interference region Ib in an integrated manner, and can change a line-of-sight direction.

According to conventional techniques, if the imaging unit 20 invades the interference region in the actual space, the movement of the imaging unit 20 is decelerated. Unfortunately, the operator may not be aware of a reason for the deceleration of the imaging unit 20 in some cases. In view of this, in a case as shown in FIG. 8 where the virtual interference region Ib in the virtual space corresponding to the interference region in the actual space is displayed on the display unit 43 and where the imaging unit model 20a is stopped inside of the virtual interference region Ib, the model moving device 42 decelerates the movement of the imaging unit 20 inside of the interference region in the actual space corresponding to the virtual interference region Ib. Such display as shown in FIG. 8 enables the operator to recognize a reason for the deceleration of the movement of the imaging unit 20. The interference region in the actual space and the virtual interference region Ib corresponding thereto can be changed in accordance with a size of the table-top 11 and a physical frame of the object P.

In Steps S2 and S4, in addition to the table-top model 11a and the imaging unit model 20a, the model moving device 42 may display a virtual interference region corresponding to a three-dimensional interference region (a region based on a position of a drape) in the vicinity of the table-top 11, in the vicinity of the table-top model 11a on the display unit 43. The drape is a cover put on the object P on the table-top 11.

Figure 9:
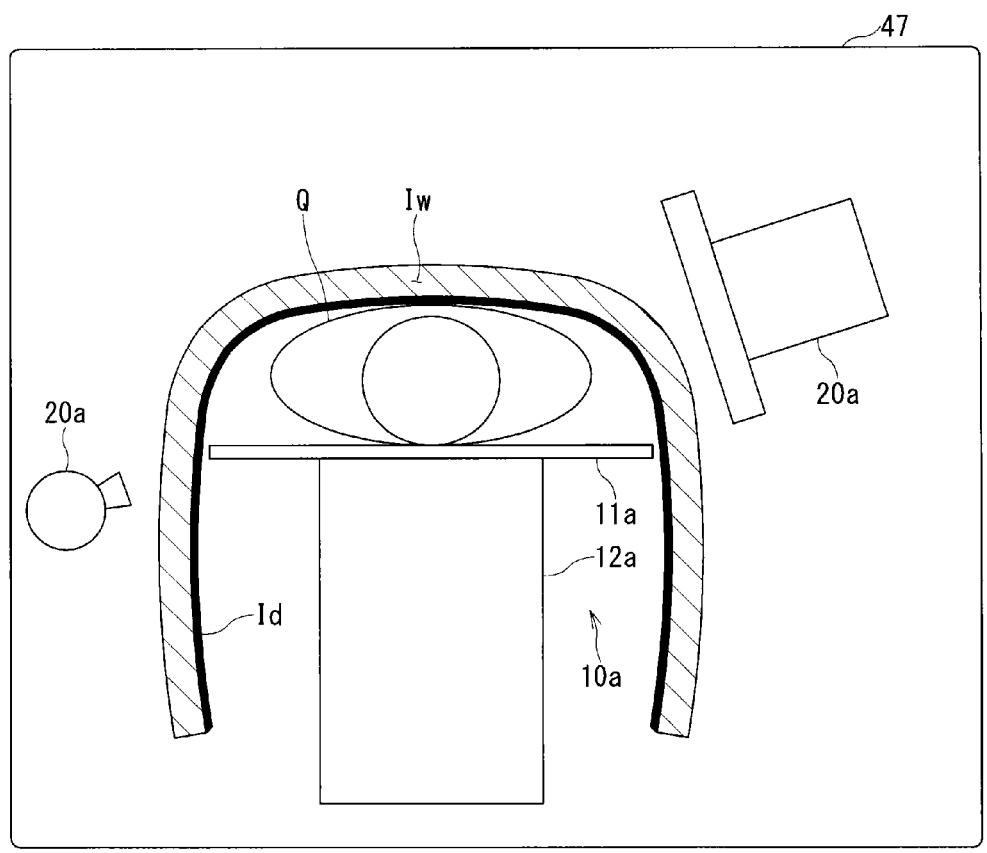
FIG. 9 is a diagram showing an example screen of the display unit on which the bed unit model and the imaging unit model arranged at the predetermined positions and the virtual interference region are displayed.

FIG. 9 is a diagram showing an example screen of the display unit 43 on which the bed unit model 10a and the imaging unit model 20a arranged at the predetermined positions and the virtual interference region are displayed. The bed unit model 10a and the imaging unit model 20a are displayed on this screen 47. A virtual drape Id corresponding to the drape in the vicinity of the table-top 11 and a virtual interference region Iw corresponding to the interference region (the region based on the position of the drape) in the vicinity of the table-top 11 are displayed in the vicinity of the table-top model 11a. The interference region (virtual interference region Iw) may be set within a given range from the drape (virtual drape Id) outside of the drape (virtual drape Id). Then, the table-top model 11a is arranged at a virtual-space position corresponding to the position of the table-top 11 so as to be movable with respect to the table-top pedestal model 12a. The imaging unit model 20a is arranged at a virtual-space position corresponding to the position of the imaging unit 20 so as to be movable with respect to the table-top pedestal model 12a.

The object Q in the virtual space corresponding to the object P (shown in FIG. 1) may be displayed on the screen 47. In response to an operation of the operator, the display unit 43 can three-dimensionally rotate the bed unit model 10a, the imaging unit model 20a, the virtual drape Id, and the virtual interference region Iw in an integrated manner, and can change a line-of-sight direction.

The table-top 11 and the object P on the table-top 11 hinders the operator who stands at an actual-space position corresponding to a position on the right side of the screen 47, from looking at the X-ray generating device 21 and understanding a positional relation between the X-ray generating device 21 and the drape, and hence the drape may be caught in the moved X-ray generating device 21. In view of this, as shown in FIG. 9, the model moving device 42 displays the virtual interference region Iw in the virtual space corresponding to the interference region in the actual space, on the display unit 43. Then, if the imaging unit model 20a is stopped inside of the virtual interference region Iw, the model moving device 42 makes a report to that effect. Such display as shown in FIG. 9 enables the operator to recognize that the imaging unit 20 is likely to be arranged at a position close to the drape, before the table-top 11 and the imaging unit 20 are moved in Step S5. Further, if the model moving device 42 makes the report before the table-top 11 and the imaging unit 20 are moved in Step S5, the operator can recognize that the imaging unit 20 is likely to be arranged at a position close to the drape.

The virtual interference region Iw on the screen 47 may be determined from the virtual drape Id based on a camera image of the drape in the actual space. Alternatively, the virtual interference region Iw on the screen 47 may be determined on the basis of the physical frame of the object P and a length in a width direction of the table-top 11.

In addition to the table-top model 11a and the imaging unit model 20a, the model moving device 42 may further display a virtual warning region corresponding to a three-dimensional warning region in the vicinity of the table-top 11, in the vicinity of the table-top model 11a on the display unit 43.

Figure 10:
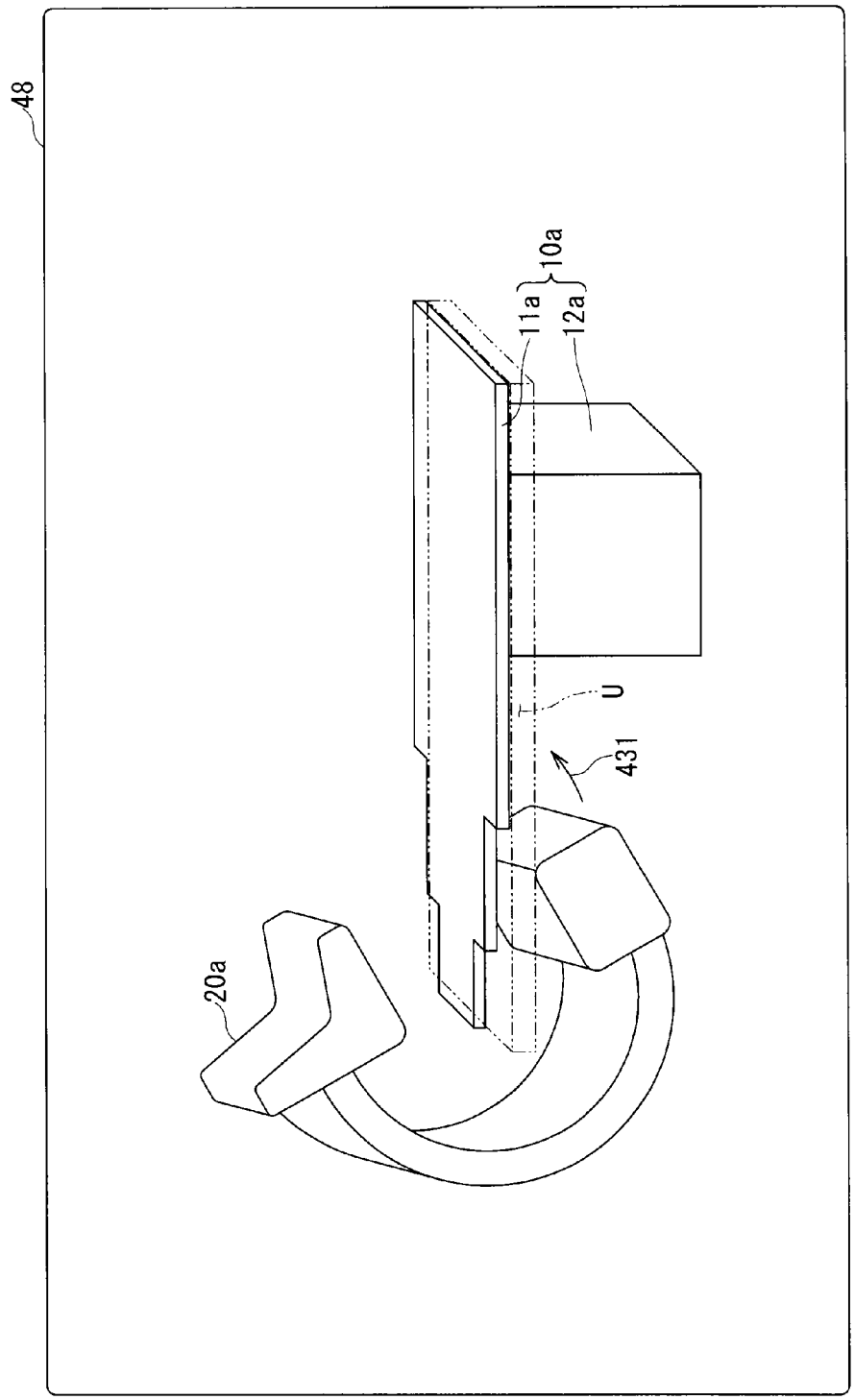
FIG. 10 is a diagram showing an example screen of the display unit on which the bed unit model and the imaging unit model arranged at the predetermined positions and a warning region are displayed.

FIG. 10 is a diagram showing an example screen of the display unit 43 on which the bed unit model 10a and the imaging unit model 20a arranged at the predetermined positions and the warning region are displayed. The bed unit model 10a and the imaging unit model 20a are displayed on this screen 48. A virtual warning region U corresponding to the warning region in the vicinity of the table-top 11 is displayed in the vicinity of the table-top model 11a. Then, the table-top model 11a is arranged at a virtual-space position corresponding to the position of the table-top 11 so as to be movable with respect to the table-top pedestal model 12a. The imaging unit model 20a is arranged at a virtual-space position corresponding to the position of the imaging unit 20 so as to be movable with respect to the table-top pedestal model 12a. In response to an operation of the operator, the display unit 43 can three-dimensionally rotate the bed unit model 10a, the imaging unit model 20a, and the virtual warning region U in an integrated manner, and can change a line-of-sight direction.

If the imaging unit model 20a is stopped inside of the virtual warning region U, the model moving device 42 reports warning information. If the imaging unit model 20a is stopped inside of the warning region U, the display unit 43 may arrange, as the warning information, an arrow 431 indicating a direction corresponding to the R1 direction in the actual space. In this case, the arrow 431 is displayed on the display unit 43 together with the bed unit model 10a and the imaging unit model 20a.

It goes without saying that the displaying methods and the reporting methods described with reference to FIG. 8 to FIG. 10 can be combined as appropriate.

In this way, in the X-ray diagnostic apparatus 100 according to the present embodiment, in response to the automatic positioning instruction after the selection instruction of the automatic mode is input from the operation unit 80, appropriate displaying and reporting are performed as needed, and the table-top 11 and the imaging unit 20 can be then moved to the imaging positions Ap1 and Ap2 in the actual space corresponding to the imaging positions Vp1 and Vp2 in the virtual space. Accordingly, in the X-ray diagnostic apparatus 100 according to the present embodiment, the table-top 11 and the imaging unit 20 can be stopped at the imaging positions Ap1 and Ap2 without interfering with each other, and a person other than the operator who performs an input operation through the operation unit 80 does not need to visually check, so that a reduction in work can be achieved.

Returning to the description of FIG. 4, if a start instruction of an imaging is input from the operation unit 80, the high voltage generating unit 50 supplies a high voltage to the X-ray generating device 21. The X-ray generating device 21 irradiates the object P put on the table-top 11 with X-rays. The X-ray detecting device 24 detects X-rays that have been transmitted through the object P, and generates X-ray projection data. The image data generating unit 60 generates image data on the basis of the X-ray projection data generated by the X-ray detecting device 24. Then, the image data generating unit 60 outputs the generated image data to the display unit 70. The display unit 70 displays the image data generated by the image data generating unit 60.

If a stop instruction of the imaging is input from the operation unit 80, the system controller 90 instructs the imaging unit 20, the moving mechanism unit 30, the modeling unit 40, the high voltage generating unit 50, and the image data generating unit 60 to end the operation, whereby the X-ray diagnostic apparatus 100 ends the operation (Step S6 in FIG. 4).

Next, the following example is described with reference to FIG. 1 to FIG. 12, and a flow chart therefor is omitted. That is, the selection instruction of the manual mode is input from the operation unit 80, and then the movement instructions of the table-top 11 and the imaging unit 20 are input from the operation unit 80. In response thereto, the table-top model 11a and the imaging unit model 20a are moved to the imaging positions in the virtual space, whereby the table-top 11 and the imaging unit 20 are moved to the imaging positions in the actual space.

If a display instruction of the bed unit model 10a and the imaging unit model 20a stored in the model storage device 41 on the display unit 43 is input from the operation unit 80, the display unit 43 displays the bed unit model 10a and the imaging unit model 20a arranged at predetermined positions in the virtual space.

If the selection instruction of the manual mode is input from the operation unit 80, and then the movement instructions of the table-top 11 and the imaging unit 20 into the respective imaging positions are input from the operation unit 80, the table-top moving mechanism 31 moves the table-top 11 from the position Ah1 in the L1 direction, and further moves the table-top 11 in the L3 direction, for example. The imaging unit moving mechanism 32 moves the imaging unit 20 from the position Ah2 in the R2 direction, for example.

The mechanism controller 33 outputs positional information of the table-top 11 and the imaging unit 20 to the system controller 90. On the basis of the actual-space positional information outputted by the mechanism controller 33, the system controller 90 calculates virtual-space positions of the table-top model 11a and the imaging unit model 20a. Then, the system controller 90 outputs the calculated virtual-space positional information to the model moving device 42.

The model moving device 42 moves the table-top model 11a and the imaging unit model 20a arranged at the positions Vh1 and Vh2 to the virtual-space positions calculated by the system controller 90, in conjunction with the table-top 11 and the imaging unit 20. In this example, the model moving device 42 moves the table-top model 11a from the position Vh1 in the direction corresponding to the L1 direction in the actual space, and further moves the table-top model 11a in the direction corresponding to the L3 direction in the actual space. The model moving device 42 moves the imaging unit model 20a from the position Vh2 in the direction corresponding to the R2 direction in the actual space.

The model moving device 42 outputs the table-top model 11a and the imaging unit model 20a that have been moved from the positions Vh1 and Vh2, to the display unit 43. The display unit 43 displays in real time the table-top model 11a and the imaging unit model 20a that have been moved from the positions Vh1 and Vh2.

Figure 11:
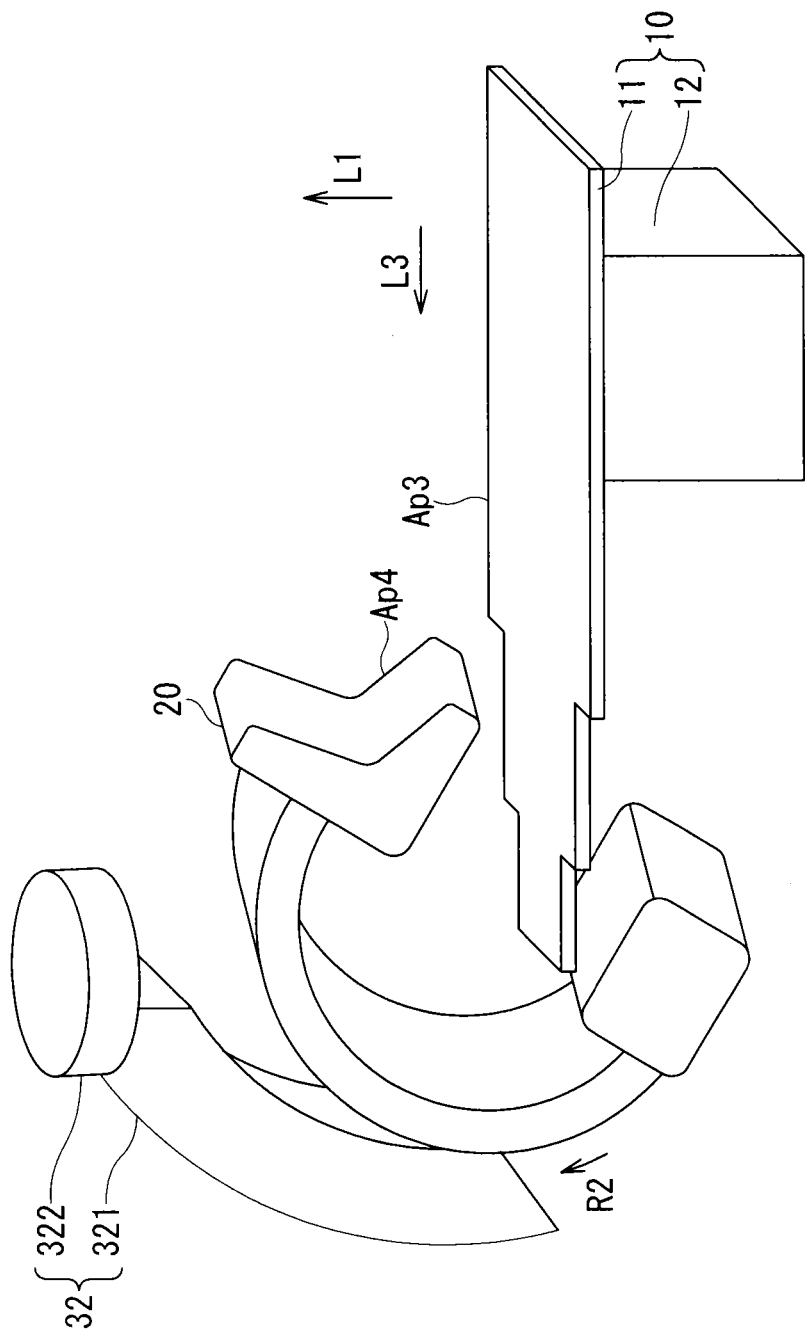
FIG. 11 is a diagram showing the table-top and the imaging unit moved to the imaging positions in the actual space.

Here, it is assumed that, in response to an instruction input from the operation unit 80, a point of view is set to a direction that enables observation of a state where one of the table-top model 11a and the imaging unit model 20a approaches another thereof and that the table-top model 11a and the imaging unit model 20a displayed on the display unit 43 are located at the imaging positions in the virtual space so as to be spaced apart from each other. In this case, if a stopping instruction of the table-top 11 and the imaging unit 20 is input from the operation unit 80, as shown in FIG. 11, the table-top moving mechanism 31 and the imaging unit moving mechanism 32 respectively stop the table-top 11 and the imaging unit 20 at imaging positions Ap3 and Ap4. FIG. 11 is a diagram showing the table-top and the imaging unit moved to the imaging positions in the actual space. In response to the stopping instruction of the table-top 11 and the imaging unit 20, the model moving device 42 stops the table-top model 11a and the imaging unit model 20a at the imaging positions in the virtual space. The display unit 43 displays the table-top model 11a and the imaging unit model 20a stopped at the imaging positions in the virtual space.

Figure 12:
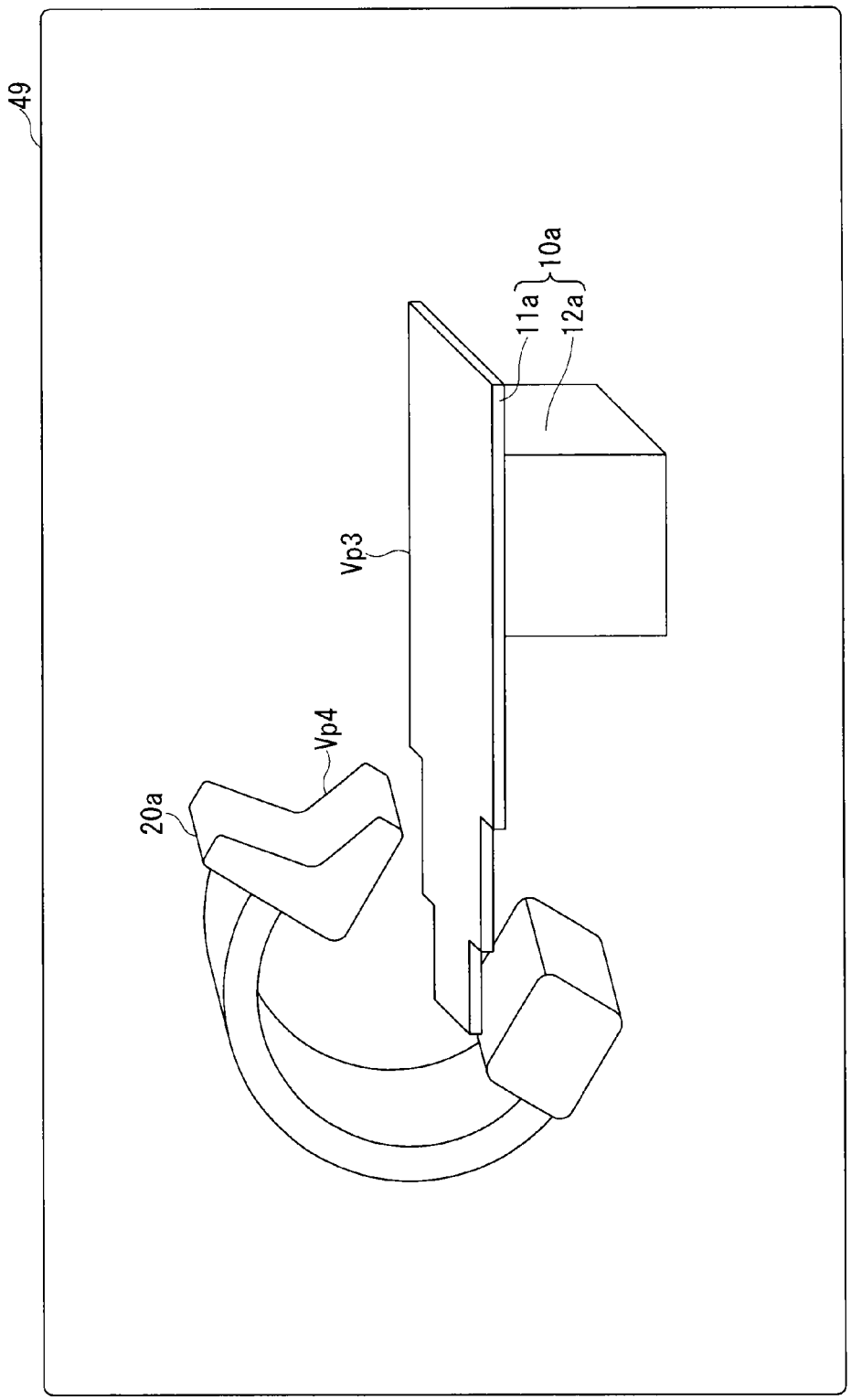
FIG. 12 is a diagram showing an example screen of the display unit on which the table-top model and the imaging unit model arranged at the imaging positions are displayed.

FIG. 12 is a diagram showing an example screen of the display unit 43 on which the table-top model 11a and the imaging unit model 20a arranged at the imaging positions are displayed. The table-top model 11a that has been moved from the position Vh1 and stopped at an imaging position Vp3 and the imaging unit model 20a that has been moved from the position Vh2 and stopped at an imaging position Vp4 are displayed on this screen 49.

In this way, in the X-ray diagnostic apparatus 100 according to the present embodiment, the table-top model 11a and the imaging unit model 20a can be moved in conjunction with the table-top 11 and the imaging unit 20, and the table-top model 11a and the imaging unit model 20a moved in conjunction with the table-top 11 and the imaging unit 20 can be displayed on the display unit 43. Then, in the X-ray diagnostic apparatus 100 according to the present embodiment, when the table-top model 11a and the imaging unit model 20a displayed on the display unit 43 are moved to the imaging positions Vp3 and Vp4 in the virtual space so as to be spaced apart from each other, the table-top 11 and the imaging unit 20 are stopped, whereby interference between the table-top 11 and the imaging unit 20 can be prevented. Accordingly, in the X-ray diagnostic apparatus 100 according to the present embodiment, a person other than the operator who performs an input operation through the operation unit 80 does not need to visually check, so that a reduction in work can be achieved.

As has been described above, in the X-ray diagnostic apparatus 100 according to the present embodiment, in response to an instruction after the selection instruction of the automatic mode is input from the operation unit 80, the table-top model 11a and the imaging unit model 20a can be moved to the imaging positions Vp1 and Vp2 in the virtual space. Subsequently, in the X-ray diagnostic apparatus 100 according to the present embodiment, the table-top model 11a and the imaging unit model 20a arranged at the imaging positions Vp1 and Vp2 are displayed from the plurality of directions on the display unit 43, whereby the operator can check whether or not the table-top model 11a and the imaging unit model 20a arranged at the imaging positions Vp1 and Vp2 interfere with each other. Then, in the X-ray diagnostic apparatus 100 according to the present embodiment, in a case where the table-top model 11a and the imaging unit model 20a at the imaging positions Vp1 and Vp2 displayed on the display unit 43 do not interfere with each other, if the automatic positioning instruction is input from the operation unit 80, the table-top 11 and the imaging unit 20 can be moved to the imaging positions Ap1 and Ap2 in the actual space corresponding to the imaging positions Vp1 and Vp2 in the virtual space.

Accordingly, in the X-ray diagnostic apparatus 100 according to the present embodiment, the table-top 11 and the imaging unit 20 (the X-ray generating device 21 and the X-ray detecting device 24) can be stopped at the imaging positions Ap1 and Ap2 without interfering with each other, and a person other than the operator who performs an input operation through the operation unit 80 does not need to visually check, so that a reduction in work can be achieved.

Meanwhile, in the X-ray diagnostic apparatus 100 according to the present embodiment, in response to an instruction after the selection instruction of the manual mode is input from the operation unit 80, the table-top model 11a and the imaging unit model 20a can be moved in conjunction with the table-top 11 and the imaging unit 20, and the table-top model 11a and the imaging unit model 20a moved in conjunction with the table-top 11 and the imaging unit 20 can be displayed on the display unit 43. Then, in the X-ray diagnostic apparatus 100 according to the present embodiment, when the table-top model 11a and the imaging unit model 20a displayed on the display unit 43 are moved to the imaging positions Vp3 and Vp4 in the virtual space so as to be spaced apart from each other, the table-top 11 and the imaging unit 20 are stopped, whereby interference between the table-top 11 and the imaging unit 20 can be prevented. Accordingly, in the X-ray diagnostic apparatus 100 according to the present embodiment, a person other than the operator who performs an input operation through the operation unit 80 does not need to visually check, so that a reduction in work can be achieved.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an imaging unit including an X-ray generating device configured to generate X-rays for irradiation of an object put on a table-top and an X-ray detecting device configured to detect the X-rays;
a moving mechanism unit configured to move the table-top and the imaging unit;
a modeling unit configured to display a table-top model representing the table-top and an imaging unit model representing the imaging unit on a display unit, and to move at least one of the table-top model and the imaging unit model on the display unit, in response to an operation of moving at least one of the table-top model and the imaging unit model; and
a mechanism controller configured to control the moving mechanism unit to move the table-top and the imaging unit in accordance with positions of the table-top model and the imaging unit model.

2. The X-ray diagnostic apparatus according to claim 1, wherein
the mechanism controller is configured to: move the table-top to a position corresponding to the position of the table-top model in response to an operation of moving the table-top model; and move the imaging unit to a position corresponding to the position of the imaging unit model in response to an operation of moving the imaging unit model.

3. The X-ray diagnostic apparatus according to claim 1, wherein
the modeling unit is configured to display a virtual interference region corresponding to an interference region in a vicinity of the table-top, in a vicinity of the table-top model in addition to the table-top model and the imaging unit model.

4. The X-ray diagnostic apparatus according to claim 3, wherein
the modeling unit is configured to display a virtual interference region suited to the object, as the virtual interference region, and
the mechanism controller is configured to control, if the imaging unit model is stopped inside of the virtual interference region, the moving mechanism unit to decelerate a moving speed of the imaging unit inside of the interference region.

5. The X-ray diagnostic apparatus according to claim 3, wherein
the modeling unit is configured to display a virtual interference region suited to a cover put on the object, as the virtual interference region, and is configured to make, if the imaging unit model is stopped inside of the virtual interference region, a report to that effect.

6. The X-ray diagnostic apparatus according to claim 1, wherein
the mechanism controller is configured to control the moving mechanism unit to move the table-top and the imaging unit, in response to an operation of moving at least one of the table-top and the imaging unit, and
the modeling unit is configured to move the table-top model and the imaging unit model to positions corresponding to positions of the table-top and the imaging unit in conjunction with the movement of the table-top and the imaging unit.

7. The X-ray diagnostic apparatus according to claim 6, wherein
the modeling unit is configured to display the table-top model and the imaging unit model moved in conjunction with the table-top and the imaging unit.

8. The X-ray diagnostic apparatus according to claim 1, wherein
the modeling unit is configured to display a virtual warning region corresponding to a warning region in a vicinity of the table-top, in a vicinity of the table-top model in addition to the table-top model and the imaging unit model, and is configured to report, if the imaging unit model is stopped inside of the virtual warning region, warning information.

* * * * *